United States Patent
Venkataraman et al.

(10) Patent No.: US 7,473,797 B2
(45) Date of Patent: Jan. 6, 2009

(54) METHODS OF 1,3-ENYNE PREPARATION USING COPPER (I) CATALYSTS

(75) Inventors: Dhandapani Venkataraman, Hadley, MA (US); Craig G. Bates, Pelham, NH (US); Pranorm Saejueng, Amherst, MA (US)

(73) Assignee: University of Massachusetts, Boston, MA (US)

( * ) Notice: Subject to any disclaimer, the term of this patent is extended or adjusted under 35 U.S.C. 154(b) by 353 days.

(21) Appl. No.: 11/115,502

(22) Filed: Apr. 27, 2005

(65) Prior Publication Data

US 2005/0255575 A1 Nov. 17, 2005

Related U.S. Application Data

(60) Provisional application No. 60/565,620, filed on Apr. 27, 2004.

(51) Int. Cl.
| | |
|---|---|
| C07C 69/76 | (2006.01) |
| C07C 67/10 | (2006.01) |
| C07C 67/04 | (2006.01) |
| C07C 13/28 | (2006.01) |
| C07C 15/67 | (2006.01) |
| C07C 1/00 | (2006.01) |
| C07C 1/20 | (2006.01) |

(52) U.S. Cl. ............... 560/104; 560/237; 560/242; 585/422; 585/446; 585/454; 585/469

(58) Field of Classification Search .......... 560/104, 560/237, 242; 585/422, 446, 454, 469
See application file for complete search history.

(56) References Cited

U.S. PATENT DOCUMENTS 7,112,697 B1 * 9/2006 Venkataraman et al. ....... 568/68

OTHER PUBLICATIONS

Marshall et al., Coupling of Alkynyl TMS Derivatives with Vinylic Iodides, Organic Letters (2001), 3 (25), 4107-4110.
Bruyere et al., Highly regioselective palladium/copper-catalyzed cross-coupling reactions of terminal alkynes and allenes, Tetrahedrom Letters (2003), 44 (48), 8669-8672.
Okuro, K; Furuune, M; Enna, M; Miura, M; Synthesis of Aryl- and Vinylacetylene Derivatives by Copper-Catalyzed Reaction of Aryl and Vinyl Iodides with Terminal Alkynes: J. Org. Chem, 1993, 4716-4721, vol. 58.
Spande, TF; Jain, P; Garraffo, HM; Pannell, LK; Yeh, HJC; Daly, JW; Fukumoto, S; Imamura, K; Tokuyama, T; Torres, JA; Snelling, RR; and Jones, TH; Occurrence and Significance of Decahydroquinolines from Dendrobatid Poison Frogs and a Myrmicine Ant: Use of 1H and 13C NMR in Their Conformational Analysis; J. Nat. Prod., 1999, 5-21, vol. 62, No. 1.
Rudi, A; Schleyer, M; and Kashman, Y; Clathculins A and B, Two Novel Nitrogen-Containing Metabolites from the Sponge Calthrina aff. reticulum; J. Nat. Prod., 2000, 1434-1436, vol. 63, No. 10.
Fontana, A; d'Ippolito, G; D'Souza, L; Mollo, E; Parameswaram, PS; and Cimino, G; New Acetogenin Peroxides from the Indian Sponge Acarnus bicladotylota; J. Nat. Prod., 2001, 131-133, vol. 64, No. 1.
El-Kaber, M'Estevez-Braun, A; Ravelo, AG; Munoz-Munoz, O; Rodriguez-Afonso, A; and Murguia, JR; Acetylenic Acids from the Aerial Parts Nanodea muscosa; J. Nat. Prod., 2003, 722-724, vol. 66, No. 5.
Hoshi, M; and Shirakawa, K; Construction of Terminal Conjugated Enynes: Regio- and Steroselective Syntheses of 3-Alken-1-ynes and 1-Trimethylsilyl-3-alken-1-ynes from Alkenyldialkylboranes and (Trimethylsilyl)ethynyl Bromide; Synlett, 2002, 1101-1104.
Negishi, E and Anastasia, L; Palladium-Catalyzed Alkynylation; Chem. Rev., 2003, 1979-2017, vol. 103, No. 5.
Saito, S and Yamamoto, Y; Recent Advances in the Transition-Metal-Catalyzed Regioselective Approaches to Polysubstituted Benzene Derivatives; Chem. Rev., 2000, 2901-2915, vol. 100, No. 8.
Zweifel, G and Polston, NL; Selective Hydroboration of Conjugated Diynes with Dialkylboranes. A Convienient Route to Conjugated cis-Enynes, $\alpha,\beta$-Acetylenic Ketones, and cis,cis-Dienes; J. of the Am Chem. Soc.; Jul. 1, 1970, 4068-4071, vol. 92, No. 13.
Rudi, A; Schleyer, M; and Kashman, Y; Clathculins A and B, Two Novel Nitrogen-Containing Metabolites from the Sponge Clathrina aff. reticulum; J. Nat. Prod., 2000, 1434-1436, vol. 63, No. 10.
Fontana, A; D'Ippolito, G; D'Souza; L; Mollo, E; Parameswaram, PS; and Cimino, G; New Acetogenin Peroxides from the Indian Sponge Acarnus bicladotylota; J. Nat. Prod., 2001, 131-133, vol. 64, No. 1.
El-Jaber, N; Estevez-Braun, A; Ravelo, AG; Munoz-Munoz; O; Rodriguez-Afonso, A; and Murguia, JR; Acethylenic Acids from the Aerial Parts Nanodea muscosa; J. Nat. Prod., 2003, 722-724; vol. 66, No. 5.
Spande, TF; Jain, P; Garraffo, HM; Pannell, LK; Yeh, HJC; and Daly, JW; Occurrence and Significance of Decahydroquinolines from Dendrobatid Poison Frogs and a Myrmicine Ant: Use of 1H and 13C NMR in Their Conformational Analysis; J. Nat. Prod., 1999, 5-21, vol. 62, No. 1.
Alami, M; Crousse, B and Ferri, F; Weakly Ligated Palladium Complexes PdCl2(RCN)2 in Piperidine: Versatile Catalysts for Sonogashira Reaction of Vinyl Chlorides at Room Temperature; Journal of Organometallic Chemistry, 2001, 114-123, vol. 624.
Alami, M and Linstrumelle, G; An Efficient Palladium-Catalyzed Reaction of Vinyl Chlorides with Terminal Acetylanes; Tetrahadron Letters, 1991, 6109-6112, vol. 32, No. 43.
Nwokogu, GC; Chemoselectivity in Palladium-Catalyzed Reactions of 2-Bromoallyl Esters; J. Org. Chem., 1985, 3900-3908-vol. 50, No. 20.

(Continued)

*Primary Examiner*—Jafar Parsa
(74) *Attorney, Agent, or Firm*—Reinhart Boerner Van Deuren s.c.

(57) ABSTRACT

A copper(I) bi-dentate ligand complex-catalyzed procedure for synthesis of 1,3-enynes. The methods and/or systems of this invention afford a variety of enynes, tolerate a variety of sensitive functional groups, and can be employed without resort to expensive palladium reagents.

20 Claims, 2 Drawing Sheets

OTHER PUBLICATIONS

Negishi, E; Qian, M; Zeng, F; Anastasia, L; and Babinski, D; Highly Statisfactory of Alkenyl Halides via Pd-Catalyzed Cross-Coupling with Alkynyzines and its Critical Comparison with the Sonogashira Alkynylation; Organic Letters, 2003, 1597-1600, vol. 5, No. 10.

Stille, JK and Simpson, JH; Sterospecific Palladium-Catalyzed Reactions of Vinyl Iodides with Acetylenic Tin Reagents; J. Am. Chem. Soc., 1987, 2138-2152, vol. 109, No. 7.

Negishi, E; Okukado, N; King, AO; Van Horn, DE; and Spiegel, BI; Double Metal Catalysis in the Cross-Coupling Reaction and its Application to the Stereo=and Regioselective Synthesis of Trisubstituted Olefins1; J. Am. Chem. Soc., Mar. 29, 1978, vol. 100, No. 7.

Miyaura, N; Yamada, K; Suginome, H; and Suzuki, A; Novel and Convenient Method for the Stereo-and Regiospecific Synthesis of Conjugated Alkadienes and Alkenyes via the Palladium-Catalyzed Cross-Coupling Reaction of 1-Alkenylboranes with Bromoalkenes and Bromoalkynes; J. Am. Chem. soc., 1985, 972-980, vol. 107, No. 4.

Ramiandrasoa, P; Brehon, B; Thivet, A; Alami, M; and Cahiez, G; An Efficient Synthesis of Stereodefined Enynes and Dienes via Pd-Catalyzed Reaction of Chloroenynes and Chlorodienes with Grignard Reagents; Tetrahedron Letters, 1997, 2447-2450, vol. 38, No. 14.

Satang, PJ and Kitamura, T; Stereoselective Formation of Conjugated Enynes via Coupling of Alkynyliodonium Tosylates and Vinylcopper Reagents; J. Am. Chem. Soc., 1987, 7561-7563, vol. 109, No. 24.

Okuro, K; Furuune, M; Enna, M; Miura; M; and Nomura, M; Synthesis of Aryl-and Vinylacetylene Derivatives by Copper-Catalyzed Reaction of Aryl and Vinyl Iodides with Terminal Alkynes; J. Org. Chem., 1993, 4716-4721, vol. 58, No. 17.

Okuro, K; Furuune, M; Miura, M and Nomura, M; Copper-Catalyzed Coupling Reaction of Aryl and Vinyl Halides with Terminal Alkynes; Tetrahedron Letters, 1992, 5363-5364, vol. 33, No. 37.

Hara, R; Liu, Y; Sun, WH; and Takahashi, T; Highly Substituted Enyne Formation by Coupling Reaction of Alkenylzirconlium Compounds with Alkynyl Halides; Tetrahedron Letters, 1997, 4103-4106, vol. 38, No. 23.

Sonogashira, K; Tohda, Y and Hagihara, N; A Convenient Synthesis of Acetylenes: Catalytic Substitutions of Acetylenic Hydrogen with Bromoalkenes, Iodoarenes, and Bromopyridines; Tetrahedron Letters, 1975, 4467-4470, No. 50.

Bates, Craig et al.: "Copper-catalyzed synthesis of 1,3-enynes"; Organic Letters, 6(9), 1441-1444 Coden: ORLEF7; ISSN: 1523-7060, 2004, XP002472599.

Okuro, Kazumi et al.: "Copper-catalyzed coupling reaction of aryl and vinyl halides with terminal alkynes"; Tetrahedron Letters, 33(37), 5363-4 Coden: Teleay; ISSN: 0040-4039, 1992, XP022084188.

Okuro, Kazumi et al.: "Synthesis of aryl-and vinylacetylene derivatives by copper-catalyzed reaction of aryl and vinyl iodides with terminal alkynes"; Journal of Organic Chemistry, 58(17), 4716-21 Coden: Joceah; ISSN: 0022-3263, 1993, XP002417738.

* cited by examiner

METHODS OF 1,3-ENYNE PREPARATION USING COPPER (I) CATALYSTS

This application claims priority benefit of U.S. application Ser. No. 60/565,620, filed Apr. 27, 2004, the entirety of which is incorporated herein by reference.

The United States government has certain rights to this invention pursuant to Grant No. CHE-0134287 from the National Science Foundation to the University of Massachusetts.

BACKGROUND OF THE INVENTION 1,3-enynes can be found in many naturally occurring and biologically active compounds. Terbinafine, which is commonly known as Lamisil®, contains the 1,3-enyne moiety and is a pharmaceutically important compound used in the treatment of superficial fungal infections. Another pharmaceutically important compound is Calicheamicin $\gamma_1^I$ which has been shown to be an effective antitumor antibiotic. 1,3-enynes are also important precursors to polysubstituted benzenes and conjugated dienes via hydroboration-protonolysis.

Among the methods developed to synthesize 1,3-enynes, the Pd—Cu catalyzed Sonogashira coupling reaction between an alkyne and a vinyl halide is most prevalent. Other methods include the Pd-catalyzed coupling between a terminal organometallic alkyne (Cu, Mg, Si, Zn, Sn) and an alkene or the alkynylation of alkenyl metals (Al, B, Cu Mg, Zr). The latter methods do suffer from some drawbacks such as use of toxic reagents, the need to prepare an organometallic alkyne or alkene, poor functional group tolerance, and undesired side-products resulting in low yields.

Various concerns in the art, however, continue to prompt development of new catalytic systems. In particular, the price of palladium is prohibitive, having risen by about 900% in recent years. Further, expensive ligands are required for the palladium reactions of interest. As a result, alternate metals and ligand systems have been the subject of increased study. One such approach uses copper to mediate the synthesis of conjugated enynes: for instance, 1,3-enynes by coupling trimethylsilyl alkynes with vinyl iodides. However, this procedure requires the use of a greater than stoichiometric amount of CuCl and is limited to propargylic alcohol derivatives. Conjugated enynes have also been prepared through the coupling of alkenyldialkylboranes and (trimethylsilyl)ethynyl bromide using catalytic Cu(acac)$_2$, but only by using strong bases such as NaOMe and LiOH. As a result, the development of copper-based protocols for such cross-coupling reactions remains an on-going concern in the art.

SUMMARY OF THE INVENTION

In light of the foregoing, it is an object of the present invention to provide one or more catalysts or catalytic systems for use in the preparation of conjugated enynes, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide a copper (I)-based ligand complex useful in conjugated enyne synthesis at catalytic and/or less than stoichiometric concentrations.

It is another object of the present invention to provide a range of Cu (I) complex catalysts and related catalytic systems for enyne synthesis, from acetylene and vinyl iodide starting materials, with complete retention of vinylic stereochemistry.

It is another object of the present invention to provide a copper (I) ligand complex catalyst and/or catalytic system for enyne synthesis from vinyl iodide and acetylene starting materials substituted with reagent-sensitive functional groups for subsequent chemical modification.

It is another object of the present invention to provide a catalyst and/or catalytic system for coupling acetylenes and vinyl iodides using solvents, reagents and/or reaction media otherwise common to or compatible with large and industrial-scale synthetic preparations.

It is another object of the present invention to provide a catalyst and/or catalytic system effective in the preparation of 1,3-enynes, without resort to palladium catalysis, over a wide range of starting materials.

Other objects, features, benefits and advantages of the present invention will be apparent from the summary and its descriptions of various embodiments, and will be readily apparent to those skilled in the art having knowledge of metal-catalyzed bond formation and coupling reactions. Such objects, features, benefits and advantages will be apparent from the above as taken into conjunction with the accompanying examples, tables, data, figures and all reasonable inferences to be drawn therefrom.

Figure 1:
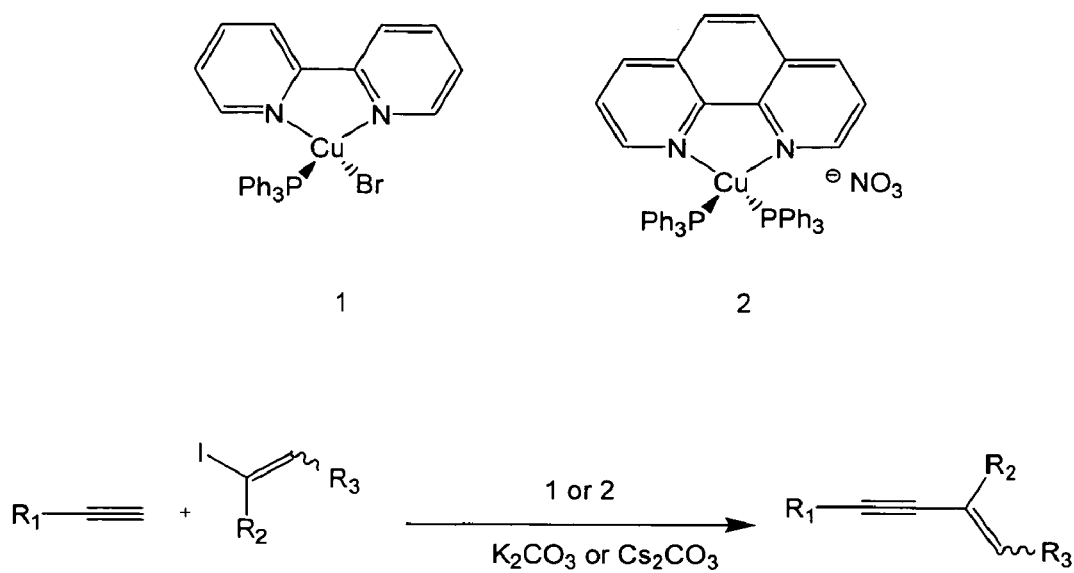
FIG. 1 shows a general reaction scheme for the preparation of 1,3-enynes, in accordance with this invention.

The present invention includes, in part, a method of using a copper (I) compound in the preparation of 1,3-enynes. Such a method comprises (1) providing a medium comprising a copper (I) bi-dentate ligand complex/compound; and (2) contacting such a medium with an acetylene compound and/or a vinyl halide compound. (See, e.g., FIG. 1.) Various copper (I) bi-dentate ligand complexes, and/or Cu (I) salts in conjunction with bi-dentate ligand components, can be employed herewith, as would be well-known to those skilled in the art made aware of this invention. Reference is made, for instance, to Table 1. More specifically, such a method can be utilized in conjunction with a range of such copper (I) ligand complexes, including but not limited to those complex compounds provided in Table 1. As used in conjunction with this invention, such complex compounds can be present in catalytic amounts, less than stoichiometric. In certain embodiments, effective levels range from about 1.0 mole percent to about about 12.0 mole percent, with reference to substrate starting materials.

Figure 2:
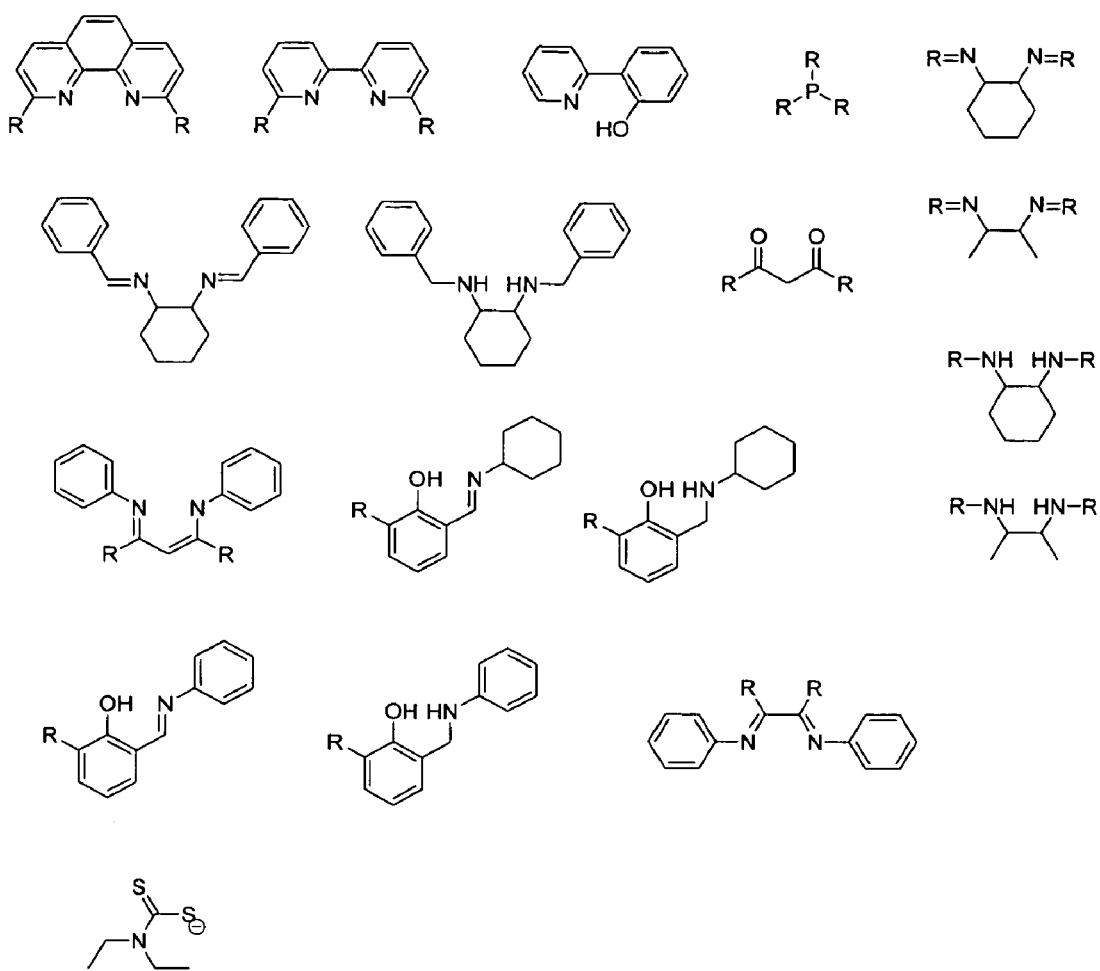
FIG. 2 provides structures of a non-limiting range of ligand components of the type useful in conjunction with the present invention, where R is without limitation and independently H, Me, Et, nBu, tBu, iPr, phenyl, aryl or cyclohexyl.

Reference is also made to FIG. 2 and the structures of non-limiting representative ligand components, either commercially available or as could be obtained via known synthetic procedures or straight-forward modifications thereof. Without limitation, in certain embodiments, ligands such as 2,2'-bipyridine and 1,10-phenanthroline can be used with good effect in conjunction with a Cu (I) metal component. Depending upon choice of reagent or starting material, such a metal-ligand compound can further comprise an alkyl or arylphosphine and/or halide and/or another counter or anionic ligand. Regardless, a base component of the aforementioned medium can comprise, in certain embodiments, cesium or potassium carbonate. In certain other embodiments, sodium tert-butoxide or potassium phosphate can be used to provide the desired coupling reaction product.

As mentioned above, the copper (I) bi-dentate ligand compounds and/or reaction products of this invention can be utilized with a range of acetylene and vinyl halide starting materials. While certain embodiments of this inventive methodology employ aryl acetylenes, various other acetylenic components can be utilized regardless of the vinyl halide. As demonstrated below, such acetylenes can be coupled, via carbon-carbon bond formation, with a diverse range of vinyl halides (e.g., substituted and unsubstituted, cyclic or acyclic). The choice of vinyl halide or acetylene is limited only by those reagents or materials commercially available or as could be obtained via known synthetic procedures or straightforward modifications thereof, as would be understood by those skilled in the art. A benefit of the present methodologies is the solubility of such Cu (I) complexes using a solvent and/or liquid medium compatible with or as currently used in preparatory or industrial scale syntheses. While toluene is used effectively, various other solvent or liquid media can be used depending upon choice of reagent and/or acetylene/vinyl starting material, required solubility and/or desired reaction parameters.

In part, the present invention can also include a method for coupling acetylenes and vinyl halides with retention of vinylic stereochemistry. Such a method comprises (1) providing a medium comprising at least one of a copper (I) bi-dentate ligand complex and the reaction product of a Cu(I) salt and a bi-dentate ligand; and (2) contacting such a medium with an acetylenic compound and/or a vinyl halide compound having either a (Z)- or (E)-configuration. Such metal-ligand compounds are as described above and illustrated below in conjunction with certain bi-dentate ligand components. Regardless of ligand identity, such Cu(I) components are useful in catalytic amounts, as compared to either the acetylene or vinyl compounds. Such a metal-ligand compound can further comprise one or more additional ligand components depending upon reagents and starting materials (e.g., triphenylphosphine and nitrate utilizing bis(triphenylphosphine) copper (I) nitrate). In the presence of a base of the type described herein, such metal-ligand compounds can be used to couple a variety of acetylenes with either (Z) or (E)-vinylhalides, with complete retention of vinylic stereochemistry.

In light of preceding, the present invention can also include a system for copper (I) catalyzed preparation of conjugated enyne compounds. Such a system can comprise a copper (I) component selected from a Cu(I) bi-dentate ligand complex, a reaction product comprising a Cu(I) salt and a bi-dentate ligand, and combinations thereof, an acetylenic compound and a vinyl halide compound in route to enyne conjugation. Such reactive interaction is departure from the prior art. Without restriction to any one mechanistic consideration or mode of operation, the results obtained herein are contrary to previous efforts. Acetylenic-alkenyl conjugation proceeds despite use of a relatively-unreactive vinyl starting material (as compared to an aryl halide) and regardless of aryl or vinyl functional groups otherwise prohibitive. However, as apparent from the data and results provided herein, the copper (I)-based interactions of this invention provide the desired conjugated enyne bond formation, over a wide range of functionalities, without resort to a palladium catalyst.

DETAILED DESCRIPTION OF CERTAIN EMBODIMENTS

To evaluate and optimize a reaction protocol in accordance herewith, the cross-coupling of phenylacetylene and (Z)-ethyl-3-iodoacrylate was chosen as a test reaction. A variety of copper(I) complexes, copper(I) salts, and copper(I) salts with certain bi-dentate ligands were examined in toluene at 110° C. with 2.0 equivalents of $Cs_2CO_3$ as a base (Table 1). Without limitation, it was found that both $[Cu(phen)(PPh_3)_2]NO_3$ and $[Cu(bipy)PPh_3Br]$ were effective at catalyzing the reaction.

Using these two bi-dentate complexes as potential catalysts, a variety of bases were screened for the cross-coupling of phenylacetylene and (Z)-ethyl-3-iodoacrylate in toluene at 110° C. for 24 hours. It was found that an effective base for use with $[Cu(phen)(PPh_3)_2]NO_3$ is $Cs_2CO_3$, as it afforded the desired product with a yield of 76% by GC. However, with $[Cu(bipy)PPh_3Br]$ as the catalyst and $K_2CO_3$ as the base, the yield was improved to 99%. Monitored over a period of time, it was discovered that the reaction was complete within 8 hours. Lowering the amount of base to 1.5 equivalents resulted in lower yields. Other bases such as $K_3PO_4$, $Na_2CO_3$, KOtBu, NaOtBu, $Et_3N$ and DBU were less effective with this particular reaction. When this particular reaction was run either in the absence of catalyst or in the absence of base the product was not observed by GC. Based on such results and control experiments, 10 mol % of $[Cu(bipy)PPh_3Br]$ as the catalyst, 2.0 equivalents of $K_2CO_3$ as the base in toluene, at 110° C., was used as part of a protocol for synthesizing 1,3-enynes.

TABLE 1

A comparison of copper(I) complexes, copper(I) salts and additives as catalysts for the cross-coupling of phenylacetylene and (Z)-ethyl-3-iodo-acrylate.*

| Catalyst | GC Yield |
|---|---|
| Well-defined complexes: | |
| $[Cu(phen)(PPh_3)_2]NO_3$ | 76% |
| $[Cu(bipy)PPh_3Br]$ | 74% |
| $[Cu(phen)PPh_3Br]$ | 69% |
| $[Cu(PPh_3)_3Br]$ | 51% |
| $[Cu(neocup)PPh_3Br]$ | 34% |
| $[Cu(acac)(PPh_3)_2]$ | 21% |
| $[Cu(neocup)_2Br]H_2O$ | 7% |
| $[Cu(CH_3CN)_4]PF_6$ | 4% |
| Copper(I) salts: | |
| CuCl | 2% |
| CuI or CuBr or $Cu_2O$ | 0% |

TABLE 1-continued

A comparison of copper(I) complexes, copper(I) salts and additives as catalysts for the cross-coupling of phenylacetylene and (Z)-ethyl-3-iodoacrylate.*

| Catalyst | GC Yield |
|---|---|
| Copper(I) salts/additives: | |
| CuI/phen/PPh$_3$(1:1:2) | 53% |
| CuI/phen(1:1) | 36% |
| CuI/bipy(1:1) | 16% |

*Reaction Conditions: 1.00 mmol phenyl acetylene, 1.00 mmol (Z)-ethyl-3-iodoacrylate, 10 mol % Cu(I) cat., 2.0 eq. Cs$_2$CO$_3$, Toluene, 110° C., 24 h. (phen = 1,10-phenanthroline, bipy = 2,2'-bipyridine, neocup = 2,9-dimethyl-1,10-phenanthroline, acac = acetylacetonate)

Using such a protocol in conjunction with (Z)-ethyl-3-iodoacrylate as a vinyl halide starting material (Table 2), it was found that wide-range of acetylenes could be coupled in good to excellent yields with complete retention of stereochemistry. This method tolerated both electron-rich and electron-poor aryl acetylenes. Sterically hindered aryl acetylenes (Table 2 entires 3 and 13) were also coupled successfully in good to excellent yields. Notably, base-sensitive functional groups such as methyl ketones (Table 2 entry 11) and methyl esters (Table 2 entires 12 and 13) were also tolerated by this methodology. A free aniline group (Table 2 entry 6), terminal alkene (Table 2 entry 7) and a bromine (Table 2 entry 16) all proved to be compatible. Heterocyclic acetylenes, such as those providing pyridine and thiophene moieties (Table 2 entries 15 and 16 respectively), were also compatible substrates; however, with the former [Cu(phen)(PPh$_3$)$_2$]NO$_3$ as the catalyst and Cs$_2$CO$_3$ base was used to obtained the cross-coupled product in a moderate yield. The cross-coupling of n-octyne and (Z)-ethyl-3-iodoacrylate demonstrated that this procedure is not restricted to aryl acetylenes (Table 2 entry 9).

TABLE 2

Copper-catalyzed cross-coupling of various acetylenes with (Z)-ethyl-3-iodoacrylate using the standard protocol.

| entry | acetylene | product | yield |
|---|---|---|---|
| 1 | phenylacetylene | EtOOC-CH=CH-C≡C-Ph (Z) | 99 |
| 2 | 4-methylphenylacetylene | EtOOC-CH=CH-C≡C-(4-MeC$_6$H$_4$) (Z) | 85 |
| 3 | 2-methoxyphenylacetylene | EtOOC-CH=CH-C≡C-(2-MeOC$_6$H$_4$) (Z) | 98 |
| 4 | 4-(methylthio)phenylacetylene | EtOOC-CH=CH-C≡C-(4-MeSC$_6$H$_4$) (Z) | 91 |

TABLE 2-continued

Copper-catalyzed cross-coupling of various acetylenes with (Z)-ethyl-3-iodoacrylate using the standard protocol.

$$R_1-\!\!\!\equiv\!\!\!-H + \underset{\text{(Z)-ethyl-3-iodoacrylate}}{I-CH=CH-COOEt} \xrightarrow[\text{Toluene, 110° C., 8 h}]{\text{10 mol \% [Cu(bipy)PPh}_3\text{Br]}\atop \text{2.0 eq K}_2\text{CO}_3} R_1-\!\!\!\equiv\!\!\!-CH=CH-COOEt$$

| entry | acetylene | product | yield |
|---|---|---|---|
| 5 | 4-(dimethylamino)phenylacetylene | (Z)-ethyl 5-(4-(dimethylamino)phenyl)pent-2-en-4-ynoate | 88 |
| 6 | 4-aminophenylacetylene | (Z)-ethyl 5-(4-aminophenyl)pent-2-en-4-ynoate | 90 |
| 7 | 4-vinylphenylacetylene | (Z)-ethyl 5-(4-vinylphenyl)pent-2-en-4-ynoate | 95 |
| 8 | 1,4-diethynylbenzene | bis-coupled product | 87[a] |
| 9 | 1-octyne | (Z)-ethyl dec-2-en-4-ynoate | 96 |
| 10 | 4-ethynylbenzonitrile | (Z)-ethyl 5-(4-cyanophenyl)pent-2-en-4-ynoate | 85 |
| 11 | 4-acetylphenylacetylene | (Z)-ethyl 5-(4-acetylphenyl)pent-2-en-4-ynoate | 92 |
| 12 | methyl 4-ethynylbenzoate | (Z)-ethyl 5-(4-(methoxycarbonyl)phenyl)pent-2-en-4-ynoate | 88 |
| 13 | methyl 2-ethynylbenzoate | (Z)-ethyl 5-(2-(methoxycarbonyl)phenyl)pent-2-en-4-ynoate | 77 |

TABLE 2-continued

Copper-catalyzed cross-coupling of various acetylenes with (Z)-ethyl-3-iodoacrylate using the standard protocol.

| entry | acetylene | product | yield |
|---|---|---|---|
| 14 | O$_2$N–C$_6$H$_4$–C≡CH | O$_2$N–C$_6$H$_4$–C≡C–CH=CH–COOEt | 89 |
| 15 | 3-ethynylpyridine | 3-pyridyl–C≡C–CH=CH–COOEt | 51[a,b] |
| 16 | 2-ethynylthiophene | 2-thienyl–C≡C–CH=CH–COOEt | 62 |
| 17 | Br–C$_6$H$_4$–C≡CH | Br–C$_6$H$_4$–C≡C–CH=CH–COOEt | 65[c] |

[a]reaction run for 12 hours,
[b]10 mol % [Cu(phen)(PPh$_3$)$_2$NO$_3$] as catalyst and 2.0 eq of Cs$_2$CO$_3$ used as base,
[c]reaction run for 20 hours.

To further assess other embodiments of this invention, cross-coupling was examined using phenyl acetylene and a variety of vinyl iodides (Table 3). The previous protocol was useful for a variety of β-(Z)-iodo-α,β-unsaturated esters. (Table 3). When (E)-ethyl-3-iodoacrylate was used as the vinyl iodide the reaction yield after 8 hours was only 55% with [Cu(bipy)PPh$_3$Br] as the catalyst and K$_2$CO$_3$ as the base. However, allowing the reaction continue for 24 hours improved the yield to 81%. A similar observation was made when (E)-1-iodo-octene was used as the vinyl iodide (Table 3 entry 5), with the yield also increased over a reaction time of 24 hours.

TABLE 3

Copper-catalyzed cross-coupling of phenylacetylene with various vinyl iodides using the standard protocol.

| entry | vinyl iodide | product | yield |
|---|---|---|---|
| 1 | (E)-ethyl-3-iodoacrylate | Ph–C≡C–CH=CH–COOEt | 81[a] |

TABLE 3-continued

Copper-catalyzed cross-coupling of phenylacetylene with various vinyl iodides using the standard protocol.

| entry | vinyl iodide | product | yield |
|---|---|---|---|
| 2 | (Z)-methyl 3-iodoacrylate | (Z)-methyl 5-phenylpent-2-en-4-ynoate | 90 |
| 3 | methyl 3-iodo-2-methylacrylate | methyl 2-methyl-5-phenylpent-2-en-4-ynoate | 97 |
| 4 | ethyl 3-iodo-3-phenylacrylate | ethyl 3-phenyl-5-phenylpent-2-en-4-ynoate | 97 |
| 5 | (E)-1-iodo-1-octene | (E)-1-phenyl-1-octen-3-yne | 99[a] |

[a] reaction run for 24 hours.

In accordance with certain embodiments of this invention, depending upon choice of starting material, changing the catalyst to [Cu(phen)(PPh$_3$)$_2$]NO$_3$ and the base to Cs$_2$CO$_3$ improved yields (Table 4). A range of electron-rich vinyl iodides were coupled in excellent yields. For instance, (E)-ethyl-3-iodoacrylate was coupled to phenyl acetylene with a near quantitative yield in 8 hours (Table 4, entry 1). The cross-coupling of both (E)-1-iodo-octene and (Z)-1-iodo-octene to phenyl acetylene (Table 4, entries 2 and 3 respectively) were complete in 8 hours with retention of stereochemistry.

TABLE 4

Copper-catalyzed cross-coupling of phenyl acetylene with various vinyl iodides using 10 mol % [Cu(phen)(PPh$_3$)$_2$]NO$_3$ as the catalyst and Cs$_2$CO$_3$ as the base.

| entry | Vinyl iodide | product | yield |
|---|---|---|---|
| 1 | (E)-ethyl 3-iodoacrylate | (E)-ethyl 5-phenylpent-2-en-4-ynoate | 99[a] |
| 2 | (E)-1-iodo-1-octene | (E)-1-phenyl-1-octen-3-yne | 98 |

TABLE 4-continued

Copper-catalyzed cross-coupling of phenyl acetylene with various
vinyl iodides using 10 mol % [Cu(phen)(PPh₃)₂]NO₃ as the catalyst and Cs₂CO₃ as the base.

| entry | Vinyl iodide | product | yield |
|---|---|---|---|
| 3 | (Z)-1-iodo-1-octene | (Z)-enyne with C₆H₁₃ | 98 |
| 4 | 1-iodo-3,4-dihydronaphthalene | Ph—≡—dihydronaphthalene | 78[b] |
| 5 | (E)-β-iodostyrene | (E)-1,4-diphenylbut-1-en-3-yne | 98 |

[a] GC yield.
[b] reaction run for 24 hours.

EXAMPLES OF THE INVENTION

The following non-limiting examples and data illustrate various aspects and features relating to the methodologies of the present invention, including the preparation of a range of diverse conjugated enyne compounds, as are available in using the catalytic systems described herein. In comparison with the prior art, the present methods, catalysts and/or catalytic systems provide results and data which are surprising, unexpected and contrary thereto. While the utility of this invention is illustrated through the use of several acetylene and vinyl iodide starting materials, copper catalysts and base components, it will be understood by those skilled in the art that comparable results are obtainable with various other acetylenes, vinyl halides and Cu(I) metal-ligand compounds, as are commensurate with the scope of this invention.

General. All of the reactions reported herein were conducted under an inert atmosphere of argon in oven-dried glassware. All reagents and solvents were obtained from Acros, Alfa Aesar or from Aldrich and were used without further purification. Potassium Carbonate (Alfa Aesar, 99%) was stored in an argon filled glove box. All vinyl iodides used are available and were synthesized using procedures previously reported in the literature. (See, e.g., Piers, E.; Wong, T.; Coish, P. D.; Rogers, C. *Can J. Chem.* 1994, 72, 1816-1819. Han, C.; Shen, R. C.; Su, S.; Porco, J. A. *Org Lett.* 2004, 6, 27-30. Lee, K.; Wiemer, D. F. *Tetrahedron Lett.* 1993, 34, 2433-2436. Brown, H. C.; Subrahmanyam, C.; Hamaoka, T.; Ravindran, N.; Bowman, D. H.; Misumi, S.; Unni, M. K.; Somayaji, V.; Bhat, N. G. *J. Org. Chem.* 1989, 54, 6068-6075.) Purification was performed by flash chromatography using ICN Flash Silica Gel, 230-400 mesh. The yields given refer to isolated yields of the characterized compounds, deemed pure by elemental analyses, $^1$H NMR and $^{13}$C NMR. In certain cases GC yields were reported. All GC yields were calculated using dodecane as an internal standard; the correction factors used to calculate the product yields were determined using an analytically pure sample. NMR spectra were recorded on a Bruker AVANCE 400 MHz spectrometer. Chemical shifts were reported in parts per million (δ). The peak patterns are indicated as follows: s, singlet; d, doublet; t, triplet; dd, doublet of doublets; dt, doublet of triplets; m, multiplet; and q, quartet. The coupling constants, J, are reported in Hertz (Hz). TMS was used as the internal reference. Elemental analyses were performed at the Microanalysis Laboratory, University of Massachusetts—Amherst. The reported melting points were uncorrected. X-ray data were collected using a Nonius kappa-CCD diffractometer with MoKa (λ=0.71073 Å) as the incident radiation. Diffraction data were collected at ambient temperature. The raw data were integrated, refined, scaled and corrected for Lorentz polarization and absorption effects, if necessary, using the programs DENZO and SCALEPAK, supplied by Nonius. Structures solutions and refinements were done (on $F_o^2$) using SIR92 and SHELXL 97 within the Nonius' MAXUS module. All structures were checked for any missing symmetry using MISSYM of PLATON. The Gas Chromatograph was a Hewlett Packard 6850 GC series with a 30-meter HP-1 100% dimethylpolysiloxane capillary column.

Synthesis of Copper(I) Complexes

A. Nitratobis(triphenylphosphine)copper(I): In an Erlenmeyer flask equipped with a Teflon-coated stir bar, methanol (100 mL) was heated to boiling and triphenylphosphine (Alfa Aesar, 24.22 g, 92.34 mmol) was slowly added to the stirring methanol. After the complete dissolution of triphenylphosphine, Cu(NO₃)₂2.5 H₂O (Fisher Scientific, 7.16 g, 30.78 mmol) was added in small portions. No special precautions were taken for the exclusion of air. Upon addition of the copper(II) nitrate, a white precipitate formed. After the completion of the addition, the contents were stirred for 30 minutes and the flask was allowed to cool to ambient temperature. The reaction mixture was then filtered through a Buchner funnel and the white residue was washed repeatedly with ethanol and then with diethyl ether. The resultant white solid was dried under dynamic vacuum to give Cu(PPh$_3$)$_2$NO$_3$ (12.378 g, 62% yield). m.p.: 238-240° C. The cell constants, contents and the space group are identical to that of the already reported structure of Cu(PPh$_3$)$_2$NO$_3$ (Cambridge Structural Database Refcode-NITPPC01).

B. Tris(triphenylphosphine)copper(I) bromide: In an Erlenmeyer flask equipped with a Teflon-coated stir bar, methanol (100 mL) was heated to boiling and triphenylphosphine (Alfa Aesar, 24.22 g, 92.34 mmol) was slowly added to the stirring methanol. After the complete dissolution of triphenylphosphine, CuBr$_2$ (Acros, 5.15 g, 23.09 mmol) was added in small portions. No special precautions were taken for the exclusion of air. Upon addition of the copper(II) bromide, a white precipitate formed. After the completion of the addition, the contents were stirred for 30 minutes and the flask was allowed to cool to ambient temperature. The reaction mixture was then filtered through a Buchner funnel and the white residue was washed repeatedly with ethanol and then with diethyl ether. The resultant white solid was dried under dynamic vacuum to give Cu(PPh$_3$)$_3$Br (20.03 g, 93% yield). m.p.: 164-166° C. The cell constants, contents and the space group are identical to that of the already reported structure of Cu(PPh$_3$)$_3$Br (Cambridge Structural Database Refcode-FEYVAG).

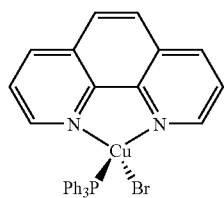

C. [Cu(phen)(PPh$_3$)Br]: In an Erlenmeyer flask equipped with a Teflon-coated magnetic stir bar, tris(triphenylphosphine)copper(I) bromide (1.40 g, 1.50 mmol) was added to chloroform (50 mL). After complete dissolution, 1,10-phenanthroline (856 mg, 1.50 mmol) was then added. The colorless solution immediately turned orange. The contents of the flask were allowed to stir for 30 minutes at room temperature. Afterwards the solvent was removed in vacuo to afford an orange solid. Recrystallization was achieved by layering 40 mL of diethyl ether onto a solution of the solid dissolved in 20 mL of dichloromethane (931 mg, 75% yield). m.p.: 252-253° C. The cell constants, contents and the space group are identical to that of the already reported structure of Cu(phen)(PPh$_3$)Br (Cambridge Structural Database Refcode-BEQLAK).

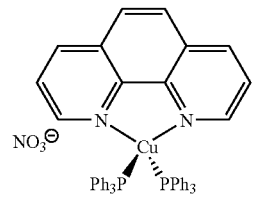

D. [Cu(phen)(PPh$_3$)$_2$]NO$_3$: In an Erlenmeyer flask equipped with a Teflon-coated magnetic stir bar, Nitratobis(triphenylphosphine)copper(I) (977 mg, 1.50 mmol) was added to chloroform (20 mL). After complete dissolution, triphenylphosphine (393 mg, 1.50 mmol), followed by 1,10-phenanthroline (270 mg, 1.50 mmol) was then added. The colorless solution immediately turned yellow. The contents of the flask were allowed to stir for 30 minutes at room temperature. Afterwards the solvent was removed in vacuo to afford a yellow solid. Recrystallization was achieved by vapor diffusion of diethyl ether into a solution of the solid dissolved in 30 mL of dichloromethane (931 mg, 75% yield). m.p.: 202-204° C.

Crystal Data for Compound D

| | |
|---|---|
| | $D_x = 1.348$ Mg m$^{-3}$ |
| C$_{48}$H$_{38}$CUN$_3$O$_3$P$_2$ | Density measured by: not measured |
| C$_{48}$H$_{38}$CUN$_3$O$_3$P$_2$ | fine-focus sealed tube |
| M$_r$ = 830.338 | Mo Kα radiation |
| Monoclinic | λ = 0.71073 |
| P2$_1$ | Cell parameters from 1928 |
| a = 10.0266 (2)Å | θ = 4.076-19.980° |
| b = 19.7098 (5)Å | μ = 0.658 mm$^{-1}$ |
| c = 10.6355 (3)Å | T = 298 K |
| α = 90.00° | Cube |
| β = 103.2034 (9)° | Yellow |
| γ = 90.00° | Crystal source: local laboratory |
| V = 2046.25 (9)Å$^3$ | |
| Z = 2 | |

Data Collection

| | |
|---|---|
| | Criterion: >2σ (I) |
| KappaCCD | θ$_{max}$ = 19.99° |
| Absorption correction: none | h = −9 → 9 |
| 3530 measured reflections | k = −18 → 18 |
| 3523 independent reflections | l = −10 → 10 |
| 3435 observed reflections | |

Refinement

| | |
|---|---|
| | R(gt) = 0.0228 |
| Refinement on F$^2$ | wR(ref) = 0.0593 |
| fullmatrix least squares refinement | wR(gt) = 0.0581 |
| R(all) = 0.0241 | S(ref) = 1.014 |
| 3523 reflections | Extinction correction: none |
| 514 parameters | Atomic scattering factors from |
| 1 restraints | International Tables Vol C Tables |
| H-atom parameters not refined | 4.2.6.8 and 6.1.1.4 |
| Calculated weights calc | Flack parameter = −0.014 (10) |
| Δ/σ$_{max}$ = 0.005 | Flack H D (1983), Acta Cryst. A39, |
| Δρ$_{max}$ = 0.115eÅ$^3$ | 876-881 |
| Δρ$_{min}$ = −0.128eÅ$^3$ | |

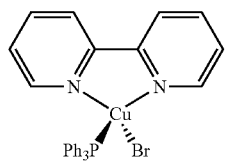

E. [Cu(bipy)(PPh$_3$)Br]: In an Erlenmeyer flask equipped with a Teflon-coated magnetic stir bar, tris(triphenylphosphine)copper(I) bromide (7.45 g, 8.00 mmol) was added to chloroform (100 mL). After complete dissolution, 2,2'-bipyridine (1.27 g, 8.00 mmol) was then added. The colorless solution immediately turned orange. The contents of the flask were allowed to stir for 30 minutes at room temperature. Afterwards the solvent was removed in vacuo to afford an orange solid. Recrystallization was achieved by layering 80 mL of diethyl ether onto a solution of the solid dissolved in 40 mL of dichloromethane (3.06 g, 68% yield). m.p.: 215-217° C. The cell constants, contents and the space group are identical to that of the already reported structure of Cu(bipy)(PPh$_3$)Br (Cambridge Structural Database Refcode-COYNOT).

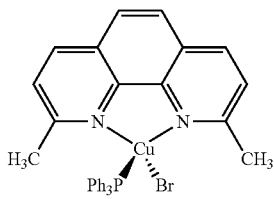

F. [Cu(neocup)(PPh$_3$)Br]: In an Erlenmeyer flask equipped with a Teflon-coated magnetic stir bar, tris(triphenylphosphine)copper(I) bromide (2.61 g, 2.73 mmol) was added to chloroform (50 mL). After complete dissolution, neocuproine (2,9-dimethyl-1,10-phenanthroline (575 mg, 2.76 mmol) was then added. The colorless solution immediately turned yellow-orange. The contents of the flask were allowed to stir for 30 minutes at room temperature. Afterwards the solvent was removed in vacuo to afford a yellow solid. Recrystallization was achieved by layering 80 mL of diethyl ether onto a solution of the solid dissolved in 40 mL of dichloromethane (1.02 g, 61% yield). m.p.: 286-288° C. The cell constants, contents and the space group are identical to that of the already reported structure of Cu(neocup)(PPh$_3$)Br.

General Synthesis of Aryl Acetylenes:

In an argon-filled glove box, Pd$_3$(dba)$_5$ (0.8 mol %), copper iodide (2.0 mol %), and triphenylphosphine (10.0 mol %) were added to a thick-walled glass tube (similar to Chemglass AF-0523) equipped with Teflon-coated stirred bar and Teflon stopper. The sealed tube was taken out of the box and under a flow of argon, triethylamine (75 mL), the bromoarene (25 mmol), and 35 mmol of trimethylsilylacetylene were added. The tube was sealed under argon and the contents were stirred at 75-80° C. for 24 h. After reaction was complete (by GC), the reaction mixture was filtered through a Buchner funnel and the residue was washed with dichloromethane until the filtrate was clear. The combined filtrate was concentrated by dynamic vacuum. The resultant yellow oil was purified by column chromatography to afford a yellow oil or light yellow solid.

Deprotection of the silyl group was accomplished by adding a small amount of potassium carbonate into solution of the protected acetylene, dissolved in a dichloromethane/methanol (30/50 mL) solution, under an argon atmosphere. The reaction mixture was stirred at room temperature for 2-3 h or until deprotection was complete (monitored by TLC). Then the reaction mixture was filtered through a Buchner funnel and the residue was washed with dichloromethane until the filtrate was clear. The solvent removed under dynamic vacuum, to afford a yellow oil or solid, which was then purified by column chromatography or filtered through a plug of silica gel. Product was analyzed (using a Direct Reading Echelle ICP) for trace amounts of Pd and none was found.

Example 1a

Synthesis of 1,3-Enynes:

General Procedure: In an argon-filled glove box, a Pyrex glass tube (2.5 cm in diameter) equipped with a Teflon-coated stir bar, was charged with potassium carbonate (Alfa Aesar, 0.553 g, 4.0 mmol) and [Cu(bipy)(PPh$_3$)Br] (10 mol % with respect to the acetylene). The tube was then sealed with a rubber septum, taken out of the glove box and toluene (4.0 mL) and 2.00 mmol of the appropriate acetylene and 2.20 mmol of the appropriate vinyl iodide were injected into the tube through the septum. The contents were then stirred at 110° C. for 8 hours unless specified otherwise. The reaction mixture was then cooled to room temperature and filtered through a pad of celite to remove any insoluble residues. The filtrate was concentrated in vacuo; the residue was purified by flash column chromatography on silica gel to obtain the analytically pure product.

Example 1b

Modified Procedure: In an argon-filled glove box, a Pyrex glass tube (2.5 cm in diameter) equipped with a Teflon-coated stir bar, was charged with cesium carbonate (Aldrich, 1.303 g, 4.0 mmol) and [Cu(phen)(PPh$_3$)$_2$NO$_3$] (10 mol % with respect to the acetylene). The tube was then sealed with a rubber septum, taken out of the glove box and toluene (4.0 mL) and 2.00 mmol of the appropriate acetylene and 2.20 mmol of the appropriate vinyl iodide were injected into the tube through the septum. The contents were then stirred at 110° C. for 8 hours unless specified otherwise. The reaction mixture was then cooled to room temperature and filtered through a pad of celite to remove any insoluble residues. The filtrate was concentrated in vacuo; the residue was purified by flash column chromatography on silica gel to obtain the analytically pure product.

Example 2a

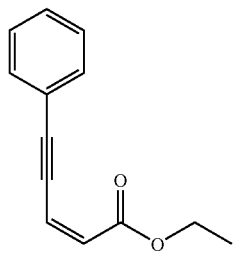

Ethyl (Z)-5-phenyl-2-buten-4-ynoate (Table 2, entry 1): The general procedure was used to convert phenylacetylene and (Z)-ethyl-3-iodoacrylate to the title product. Purification by flash chromatography (15% ethyl acetate in hexanes as the eluent) gave the analytically pure product as a light yellow oil (396 mg, 99% yield). $^1$H NMR (400 MHz, CDCl$_3$) δ 7.54-7.52 (m, 2H), 7.34 (m, 3H), 6.36 (d, J=11.43, 1H), 6.12 (d, J=11.42, 1H), 4.26 (q, 2H), 1.33 (t, 3H). $^{13}$C NMR (100 MHz, CDCl$_3$) δ 164.72, 131.96, 129.10, 128.30, 128.17, 122.75, 122.57, 101.10, 86.30, 60.36, 14.23. Anal. Calc'd. for C$_{13}$H$_{12}$O$_2$: C, 77.98; H, 6.04; Found C, 77.78; H, 6.06.

Example 2b

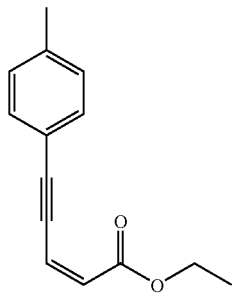

5-p-Tolyl-pent-2-en-4-ynoic acid ethyl ester (Table 2, entry 2): The general procedure was used to convert 1-Ethynyl-4-methyl-benzene and (Z)-ethyl-3-iodoacrylate to the title product. Purification by flash chromatography (10% ethyl acetate in hexane as the eluent) gave the analytically pure product as a light yellow oil (350 mg, 85% yield). $^1$H NMR (400 MHz, CDCl$_3$) δ 7.43-7.41 (d, J=8.1, 2H), 7.16-7.14 (d, J=7.9, 2H), 6.37-6.34 (d, J=11.4, 1H), 6.12-6.09 (d, J=11.4, 1H), 4.29-4.23 (q, J=7.1, 2H), 2.36 (s, 3H), 1.35-1.31 (t, J=7.1, 3H). $^{13}$C NMR (100 MHz, CDCl$_3$) δ 164.92, 139.62, 132.12, 129.28, 127.83, 123.14, 119.76, 101.77, 86.19, 60.44, 21.66, 14.42. Anal. Calcd. for C$_{14}$H$_{14}$O$_2$: C, 78.48; H, 6.59; Found C, 78.22; H, 6.78.

Example 2c

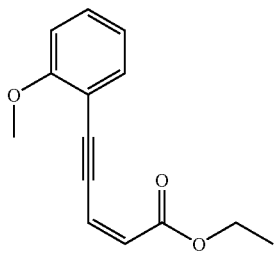

5-(2-Methoxy-phenyl)-pent-2-en-4-ynoic acid ethyl ester (Table 2, entry 3): The general procedure was used to convert 1-Ethynyl-2-methoxy-benzene and (Z)-ethyl-3-iodoacrylate to the title product. Purification by flash chromatography (20% ethyl acetate in hexane as the eluent) gave the analytically pure product as a light yellow oil (480 mg, 98% yield). $^1$H NMR (400 MHz, CDCl$_3$) δ 7.52-7.50 (dd, J=7.5, 1.7, 1H), 7.33-7.29 (m, 1H), 6.93-6.89 (dt, J=7.6, 0.9, 1H), 6.88-6.86 (d, J=8.3, 1H), 6.42-6.39 (d, J=11.4, 1H), 6.11-6.08 (d, J=11.4, 1H), 4.28-4.22 (q, J=7.1, 2H), 3.88 (s, 3H), 1.33-1.29 (t, J=7.1, 3H). $^{13}$C NMR (100 MHz, CDCl$_3$) δ 164.86, 160.32, 134.25, 130.84, 127.67, 123.10, 120.54, 111.96, 110.73, 97.93, 90.45, 60.32, 55.81, 14.28. Anal. Calcd. for C$_{14}$H$_{14}$O$_3$: C, 73.03; H, 6.13; Found C, 73.08; H, 6.19.

Example 2d

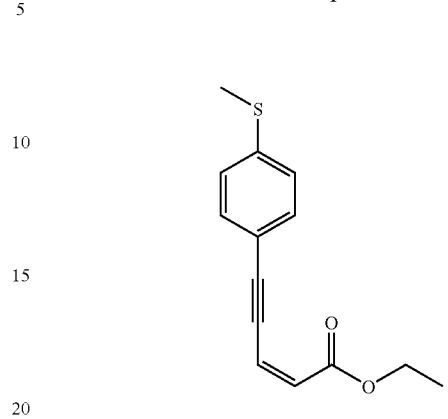

5-(4-Methylsulfanyl-phenyl)-pent-2-en-4-ynoic acid ethyl ester (Table 2, entry 4): The general procedure was used to convert 1-Ethynyl-4-methylsulfanyl-benzene and (Z)-ethyl-3-iodoacrylate to the title product. Purification by flash chromatography (20% ethyl acetate in hexane as the eluent) gave the analytically pure product as a light yellow oil (450 mg, 91% yield). $^1$H NMR (400 MHz, CDCl$_3$) δ 7.44-7.42 (d, J=8.5, 2H), 7.18-7.16 (d, J=8.5, 2H), 6.35-6.32 (d, J=11.4, 1H), 6.11-6.09 (d, J=11.4, 1H), 4.28-4.22 (q, J=7.1, 2H), 2.46 (s, 3H), 1.34-1.30 (t, J=7.1, 3H). $^{13}$C NMR (100 MHz, CDCl$_3$) δ 164.81, 140.87, 132.33, 127.85, 125.68, 122.81, 118.84, 101.21, 86.77, 60.37, 15.16, 14.32. Anal. Calcd. for C$_{14}$H$_{14}$O$_2$S: C, 68.26; H, 5.73; S, 13.02; Found C, 68.50; H, 5.88; S, 13.18.

Example 2e

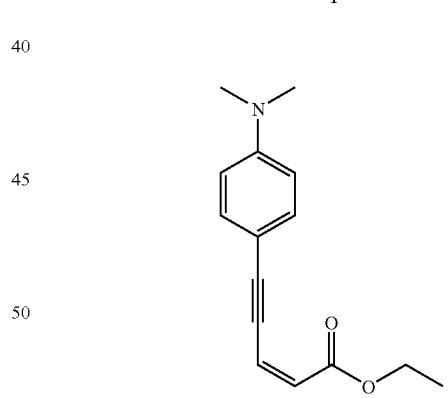

5-(4-Dimethylamino-phenyl)-pent-2-en-4-ynoic acid ethyl ester (Table 2, entry 5): The general procedure was used to convert 1(4-Ethynyl-phenyl)-dimethyl-amine and (Z)-ethyl-3-iodoacrylate to the title product. Purification by flash chromatography (10% ethyl acetate in hexane as the eluent) gave the analytically pure product as a yellow solid (420 mg, 88% yield). $^1$H NMR (400 MHz, CDCl$_3$) δ 7.42-7.39 (d, J=8.9, 2H), 6.62-6.60 (d, J=9.0, 2H), 6.37-6.34 (d, J=11.4, 1H), 6.01-5.98 (d, J=11.4, 1H), 4.28-4.22 (q, J=7.1, 2H), 2.97 (s, 6H), 1.35-1.31 (t, J=7.1, 3H). $^{13}$C NMR (100 MHz, CDCl$_3$) δ 165.15, 150.62, 133.53, 125.21, 123.63, 111.48, 108.97, 104.06, 85.92, 60.08, 39.94, 14.28. Anal. Calcd. for $C_{15}H_{17}NO_2$: C, 74.05; H, 7.04; N, 5.76; Found C, 74.29; H, 7.20; N, 5.71. m.p.: 58.0°-59.5° C.

Example 2f

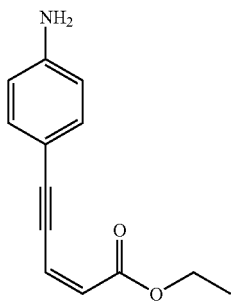

5-(4-Amino-phenyl)-pent-2-en-4-ynoic acid ethyl ester (Table 2, entry 6): The general procedure was used to convert 4-Ethynyl-phenylamine and (Z)-ethyl-3-iodoacrylate to the title product. Purification by flash chromatography (30% ethyl acetate in hexane as the eluent) gave the analytically pure product as a light yellow oil (350 mg, 90% yield). $^1$H NMR (400 MHz, CDCl$_3$) δ 7.34-7.32 (d, J=8.4, 2H), 6.60-6.58 (d, J=8.4, 2H), 6.36-6.34 (d, J=11.4, 1H), 6.05-6.02 (d, J=11.4, 1H), 4.28-4.23 (q, J=7.1, 2H), 3.96 (s, 2H), 1.35-1.31 (t, J=7.1, 3H). $^{13}$C NMR(100 MHz, CDCl$_3$) δ 165.21, 148.01, 133.78, 125.92, 123.66, 114.54, 111.33, 103.46, 85.59, 60.28, 14.32. Anal. Calcd. for $C_{13}H_{13}NO_2$: C, 72.54; H, 6.09; N, 6.51; Found C, 72.63; H, 6.26; N, 6.32.

Example 2g

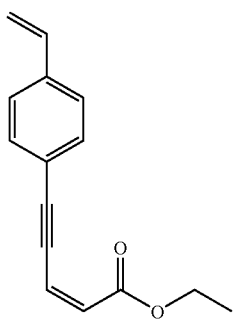

5-(4-Vinyl-phenyl)-pent-2-en-4-ynoic acid ethyl ester (Table 2, entry 7): The general procedure was used to convert 1-Ethynyl-4-vinyl-benzene and (Z)-ethyl-3-iodoacrylate to the title product. Purification by flash chromatography (10% ethyl acetate in hexane as the eluent) gave the analytically pure product as a light yellow oil (420 mg, 95% yield). $^1$H NMR (400 MHz, CDCl$_3$) δ 7.51-7.49 (d, J=8.3, 2H), 7.39-7.37 (d, J=8.3, 2H), 6.73-6.66 (dd, J=17.5, 10.8, 1H), 6.38-6.35 (d, J=11.4, 1H), 6.14-6.12 (d, J=11.4, 1H), 5.81-5.77 (d, J=17.6, 1H), 5.33-5.30 (d, J=10.9, 1H), 4.29-4.24 (q, J=7.1, 2H), 1.35-1.32 (t, J=7.1, 3H). $^{13}$C NMR (100 MHz, CDCl$_3$) δ 164.92, 139.62, 132.12, 129.28, 127.83, 123.14, 119.76, 101.77, 86.19, 60.44, 21.66, 14.42. Anal. Calcd. for $C_{14}H_{14}O_2$: C, 79.62; H, 6.24; Found C, 79.37; H, 6.48.

Example 2h

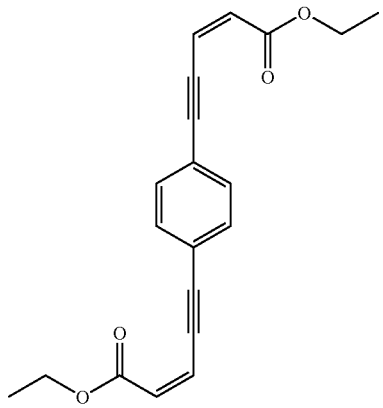

5-[4-(4-Ethoxycarbonyl-but-3-en-1-ynyl)-phenyl]-pent-2-en-4-ynoic acid ethyl ester (Table 2, entry 8): The general procedure was used to convert 1,4-Diethynyl-benzene and (Z)-ethyl-3-iodoacrylate to the title product in 12 hours. Purification by flash chromatography (10% ethyl acetate in hexane as the eluent) gave the analytically pure product as a light yellow solid (560 mg, 87% yield). $^1$H NMR (400 MHz, CDCl$_3$) δ 7.50 (s, 4H), 6.37-6.34 (d, J=11.4, 2H), 6.17-6.14 (d, J=11.4, 2H), 4.28-4.23 (q, J=7.1, 4H), 1.34-1.30 (t, J=7.1, 6H). $^{13}$C NMR (100 MHz, CDCl$_3$) δ 164.57, 131.88, 128.72, 123.31, 122.34, 100.27, 88.36, 60.39, 14.21. Anal. Calcd. for $C_{20}H_{18}O_4$: C, 74.52; H, 5.63; Found C, 74.33; H, 5.71. m.p.: 73.0°-74.0° C.

Example 2i

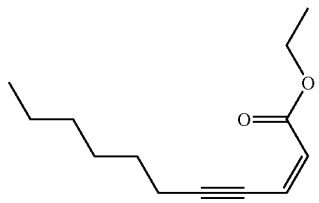

(Z)-ethyl undec-2-en-4-ynoate (Table 2. entry 9): The general procedure was used to convert n-octyne and (Z)-ethyl-3-iodoacrylate to the title product. Purification by flash chromatography (5% ethyl acetate in hexane as the eluent) gave the analytically pure product as a light yellow oil (401 mg, 96% yield). $^1$H NMR (400 MHz, CDCl$_3$) δ 6.13 (dt, J=10.82, 1H), 6.02 (d, J=10.96, 1H), 4.21 (q, 2H), 2.44 (m, 2H), 1.58 (p, 2H), 1.42 (m, 2H), 1.30-1.28 (m, 7H), 0.89 (t, 3H). $^{13}$C NMR (100 MHz, CDCl$_3$) δ 164.87, 127.34, 123.89, 104.17, 77.66, 60.18, 31.30, 28.60, 28.36, 22.49, 20.07, 14.21, 13.99. Anal. Calcd. for $C_{13}H_{20}O_2$: C, 74.96; H, 9.68; Found C, 74.96; H, 9.56.

Example 2j

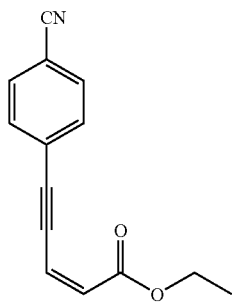

5-(4-Cyano-phenyl)-pent-2-en-4-ynoic acid ethyl ester (Table 2, entry 10): The general procedure was used to convert 4-Ethynyl-Bezonitrile and (Z)-ethyl-3-iodoacrylate to the title product. Purification by flash chromatography (20% ethyl acetate in hexane as the eluent) gave the analytically pure product as a light yellow solid (380 mg, 85% yield). $^1$H NMR (400 MHz, CDCl$_3$) δ 7.64-7.59 (m, J=8.5, 4H), 6.37-6.34 (d, J=11.3, 1H), 6.24-6.21 (d, J=11.3, 1H), 4.28-4.23 (q, J=7.1, 2H), 1.34-1.30 (t, J=7.1, 3H). $^{13}$C NMR (100 MHz, CDCl$_3$) δ 164.40, 132.39, 132.03, 130.08, 127.49, 121.74, 118.25, 112.37, 98.34, 89.94, 60.57, 14.23. Anal. Calcd. for $C_{14}H_{11}NO_2$: C, 74.65; H, 4.92, N, 6.22; Found C, 74.45; H, 4.84, N, 6.06. m.p.: 69.5°-71.5° C.

Example 2k

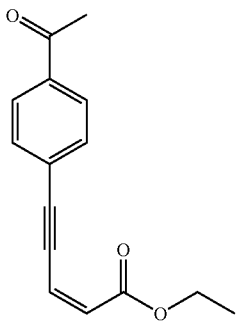

5-(4-Acetyl-phenyl)-pent-2-en-4-ynoic acid ethyl ester (Table 2, entry 11): The general procedure was used to convert 1-(4-Ethynyl-phenyl)-ethanone and (Z)-ethyl-3-iodoacrylate to the title product. Purification by flash chromatography (440 mg, 20% ethyl acetate in hexane as the eluent) gave the analytically pure product as a light yellow oil (92% yield). $^1$H NMR (400 MHz, CDCl$_3$) δ 7.93-7.90 (d, J=8.5, 2H), 7.60-7.58 (d, J=8.5, 2H), 6.38-6.35 (d, J=11.4, 1H), 6.20-6.18 (d, J=11.4, 1H), 4.28-4.23 (q, J=7.1, 2H), 2.58 (s, 3H), 1.34-1.30 (t, J=7.1, 3H). $^{13}$C NMR (100MHz, CDCl$_3$) δ 197.09, 164.54, 136.87, 132.09, 129.43, 128.24, 127.39, 122.22. 99.65, 89.11, 60.53, 26.59, 14.29. Anal. Calcd. for $C_{15}H_{14}O_3$: C, 74.36; H, 5.82; Found C, 74.31; H, 5.97.

Example 2l

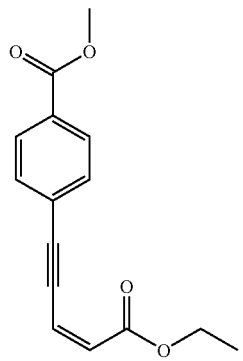

4-(4-Ethoxycarbonyl-but-3-en-1-ynyl)-benzoic acid methyl ester (Table 2, entry 12): The general procedure was used to convert 4-Ethynyl-benzoic acid methyl ester and (Z)-ethyl-3-iodoacrylate to the title product. Purification by flash chromatography (30% ethyl acetate in hexane as the eluent) gave the analytically pure product as a light yellow solid (450 mg, 88% yield). $^1$H NMR (400 MHz, CDCl$_3$) δ 8.01-7.99 (d, J=8.5, 2H), 7.59-7.57 (d, J=8.5, 2H), 6.37-6.34 (d, J=11.4, 1H), 6.20-6.17 (d, J=11.4, 1H), 4.29-4.23 (q, J=7.1, 2H), 3.91 (s, 3H), 1.34-1.30 (t, J=7.1, 3H). $^{13}$C NMR (100 MHz, CDCl$_3$) δ 166.36, 164.60, 131.91, 130.31, 129.52, 129.37, 127.29, 122.25, 99.73, 88.79, 60.55, 52.24, 14.30. Anal. Calcd. for $C_{15}H_{14}O_4$: C, 69.76; H, 5.46; Found C, 69.90; H, 5.55. m.p.: 49.0°-51.0° C.

Example 2m

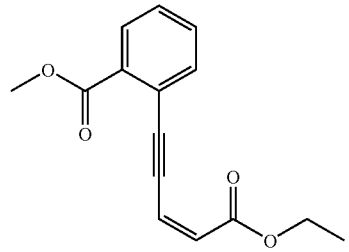

2-(4-Ethoxycarbonyl-but-3-en-1-ynyl)-benzoic acid methyl ester (Table 2, entry 13): The general procedure was used to convert 2-Ethynyl-benzoic acid methyl ester and (Z)-ethyl-3-iodoacrylate to the title product. Purification by flash chromatography (20% ethyl acetate in hexane as the eluent) gave the analytically pure product as a light yellow oil (410 mg, 77% yield). $^1$H NMR (400 MHz, CDCl$_3$) δ 7.96-7.95 (d, J=7.8, 1H), 7.70-7.68 (d, J=8.2, 1H), 7.50-7.46 (t, J=7.5, 1H), 7.37-7.41 (t, J=7.7, 1H), 6.46-6.43 (d, J=11.4, 1H), 6.18-6.15 (d, J=11.4, 1H), 4.27-4.21 (q, J=7.1, 2H), 3.92 (s, 3H), 1.31-1.27 (t, J=7.1, 3H). $^{13}$C NMR (100 MHz, CDCl$_3$) δ 166.31, 164.65, 134.69, 131.79, 131.74, 130.42, 128.73, 128.70, 123.23, 122.91, 99.64, 90.93, 60.40, 52.23, 14.27. Anal. Calcd. for $C_{15}H_{14}O_4$: C, 69.76; H, 5.46; Found C, 69.93; H, 5.59.

Example 2n

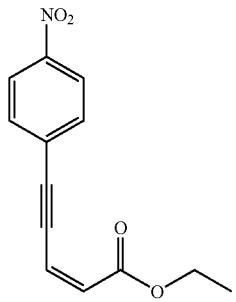

5-(4-Nitro-phenyl)-pent-2-en-4-ynoic acid ethyl ester (Table 2, entry 14): The general procedure was used to convert 1-Ethynyl-4-nitro-benzene and (Z)-ethyl-3-iodoacrylate to the title product except using 1.6 mmol of acetylene and 1.8 mmol vinyl iodide. Purification by flash chromatography (20% ethyl acetate in hexane as the eluent) gave the analytically pure product as a yellow solid (350 mg, 89% yield). $^1$H NMR (400 MHz, $CDCl_3$) δ 8.22-8.19 (d, J=8.9, 2H), 7.68-7.65 (d, J=8.9, 2H), 6.38-6.35 (d, J=11.4, 1H), 6.26-6.23 (d, J=11.4, 1H), 4.29-4.24 (q, J=7.1, 2H), 1.35-1.31 (t, J=7.1, 3H). $^{13}$C NMR (100 MHz, $CDCl_3$) δ 164.38, 147.48, 132.66, 130.32, 129.41, 123.57, 121.67, 97.99, 90.64, 60.64, 14.23. Anal. Calcd. for $C_{13}H_{11}NO_4$: C, 63.67; H, 4.52; N, 5.71; Found C, 63.45; H, 4.44; N, 5.65. m.p.: 76.0°-78.0° C.

Example 2o

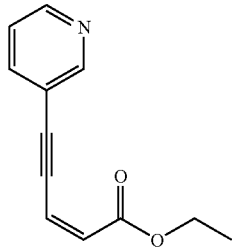

5-Pyridin-3-yl-pent-2-en-4-ynoic acid ethyl ester (Table 2, entry 15): The modified procedure was used to convert 3-Ethynyl-pyridine and (Z)-ethyl-3-iodoacrylate to the title product in 12 hours. Purification by flash chromatography (30% ethyl acetate in hexane as the eluent) gave the analytically pure product as a light yellow oil (200 mg, 51% yield). $^1$H NMR (400 MHz, $CDCl_3$) δ 8.76 (s, 1H), 8.57-8.55 (dd, J=4.9, 1.5, 1H), 7.82-7.79 (td, J=7.8, 1.8, 1H), 7.29-7.26 (m, 1H), 6.38-6.35 (d, J=11.4, 1H), 6.21-6.18 (d, J=11.4, 1H), 4.29-4.23 (q, J=7.1, 2H), 1.34-1.31 (t, J=7.1, 3H). $^{13}$C NMR (100 MHz, $CDCl_3$) δ 164.32, 152.25, 149.13, 138.58, 129.22, 122.86, 121.80, 119.68, 96.97, 89.03, 60.34, 14.08. Anal. Calcd. for $C_{12}H_{11}NO_2$: C, 71.63; H, 5.51; N, 6.96; Found C, 71.77; H, 5.64; N, 6.73.

Example 2p

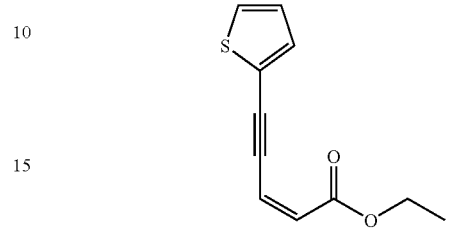

5-Thiophen-2-yl-pent-2-en-4-ynoic acid ethyl ester (Table 2, entry 16): The general procedure was used to convert 2-Ethynyl-thiophene and (Z)-ethyl-3-iodoacrylate to the title product. Purification by flash chromatography (10% ethyl acetate in hexane as the eluent) gave the analytically pure product as a light yellow oil (230 mg, 62% yield). $^1$H NMR (400 MHz, $CDCl_3$) δ 7.36-7.35 (dd, J=5.1, 1.0, 1H), 7.33-7.32 (dd, J=3.6, 1.0, 1H), 7.02-7.00 (m, 1H), 6.36-6.33 (d, J=11.4, 1H), 6.10-6.08 (d, J=11.4, 1H), 4.29-4.23 (q, J=7.1, 2H), 1.36-1.32 (t, J=7.1, 3H). $^{13}$C NMR (100 MHz, $CDCl_3$) δ 164.79, 133.49, 129.19, 127.62, 127.36, 122.57, 122.29, 94.50, 90.82, 60.51, 14.31. Anal. Calcd. for $C_{11}H_{10}O_2S$: C, 64.05; H, 4.89; S, 15.55; Found C, 64.01; H, 4.95; S, 15.27.

Example 2q

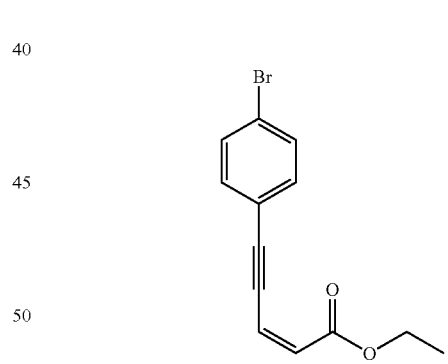

5-(4-Bromo-phenyl)-pent-2-en-4-ynoic acid ethyl ester (Table 2, entry 17): The general procedure was used to convert 1-Bromo-4-ethynyl-benzene and (Z)-ethyl-3-iodoacrylate to the title product in 20 hours. Purification by flash chromatography (355 mg, 20% ethyl acetate in hexane as the eluent) gave the analytically pure product as a light yellow oil (65% yield). $^1$H NMR (400 MHz, $CDCl_3$) δ 7.48-7.46 (d, J=8.5, 2H), 7.39-7.36 (d, J=8.5, 2H), 6.33-6.30 (d, J=11.4, 1H), 6.16-6.13 (d, J=11.4, 1H), 4.27-4.22 (q, J=7.1, 2H), 1.33-1.29 (t, J=7.1, 3H). $^{13}$C NMR (100 MHz, $CDCl_3$) δ 164.64, 133.40, 131.68, 128.69, 123.61, 122.49, 121.60, 99.81, 87.38, 60.46, 14.29. Anal. Calcd. for $C_{13}H_{11}BrO_2$: C, 55.94; H, 3.97; Br, 28.63; Found C, 56.05; H, 4.07; Br, 27.6.

Example 3a

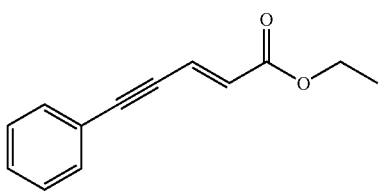

Ethyl (E)-5-phenyl-2-buten-4-ynoate (Table 3, entry 1): The general procedure was used to convert phenylacetylene and (E)-ethyl-3-iodoacrylate to the title product in 24 hours. Purification by flash chromatography (10% ethyl acetate in hexanes as the eluent) gave the analytically pure product as a light yellow oil (325 mg, 81% yield). $^1$H NMR (400 MHz, CDCl$_3$) δ 7.47 (m, 2H), 7.35 (m, 3H), 6.98 (d, J=15.84, 1H), 6.30 (d, J=15.84, 2H), 4.24 (q, 2H), 1.31 (t, 3H). $^{13}$C NMR (100 MHz, CDCl$_3$) δ 165.84, 131.91, 130.01, 129.24, 128.41, 125.01, 122.162, 98.20, 86.32, 60.72, 14.19. Anal. Calc'd. for $C_{13}H_{12}O_2$: C, 77.98; H, 6.04; Found C, 78.06; H, 6.13.

Example 3b

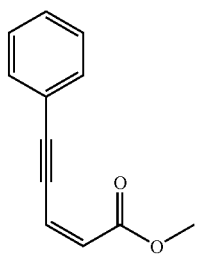

Methyl (Z)-5-phenyl-2-penten-4-ynoate (Table 3, entry 2): The general procedure was used to convert phenylacetylene and (Z)-methyl-3-iodoacrylate to the title product. Purification by flash chromatography (15% ethyl acetate in hexanes as the eluent) gave the analytically pure product as a light yellow oil (336 mg, 90% yield). $^1$H NMR (400 MHz, CDCl$_3$) δ 7.54 (m, 2H), 7.35 (m, 3H), 6.36 (d, J=11.39, 1H), 6.14 (d, J=11.41, 1H), 3.80 (s, 3H). $^{13}$C NMR (100 MHz, CDCl$_3$) δ 165.25, 132.16, 129.28, 128.42, 127.79, 123.22, 122.63, 101.45, 86.37, 51.55. Anal. Calc'd. for $C_{12}H_{10}O_2$: C, 77.40; H, 5.41; Found C, 77.41; H, 5.35.

Example 3c

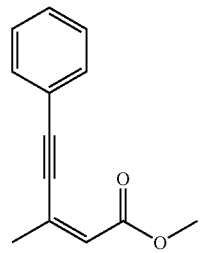

cis-3-methyl-5-phenyl-pent-2-en-4-ynoic acid methyl ester (Table 3, entry 3): The general procedure was used to convert phenylacetylene and (Z)-β-Iodo-β-methyl methyl acrylate to the title product. Purification by flash chromatography (15% ethyl acetate in hexanes as the eluent) gave the analytically pure product as a light yellow oil (388 mg, 97% yield). $^1$H NMR (400 MHz, CDCl$_3$) δ 7.55 (m, 2H), 7.33 (m, 3H), 6.03 (q, 1H), 3.76 (s, 3H), 2.13 (d, J=1.45, 3H). $^{13}$C NMR(100 MHz, CDCl$_3$) δ 165.42, 134.99, 132.03, 129.02, 128.29, 123.85, 122.65, 100.31, 88.25, 51.23, 25.11. Anal. Calc'd. for $C_{13}H_{12}O_2$: C, 77.98; H, 6.04; Found C, 77.83; H, 6.04.

Example 3d

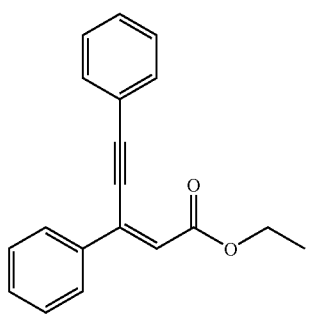

(Z)-ethyl 3,5-diphenylpent-2-en-4-ynoate (Table 3, entry 4): The general procedure was used to convert phenylacetylene and (Z)-ethyl 3-iodo-3-phenylacrylate to the title product. Purification by flash chromatography (5% ethyl acetate in hexanes as the eluent) gave the analytically pure product as a light yellow oil (530 mg, 96% yield). $^1$H NMR (400 MHz, CDCl$_3$) δ 7.78 (m, 2H), 7.63 (m, 2H), 7.38 (m, 6H), 6.59 (s, 1H), 2.06 (q, 2H), 1.35 (t, 3H). $^{13}$C NMR (100 MHz, CDCl$_3$) δ 165.12, 136.92, 136.08, 131.85, 129.66, 128.99, 128.42, 128.18, 126.96, 122.54, 122.48, 101.88, 86.68, 60.16, 14.17. Anal. Calc'd. for $C_{19}H_{16}O_2$: C, 82.58; H, 5.84; Found C, Example 3e

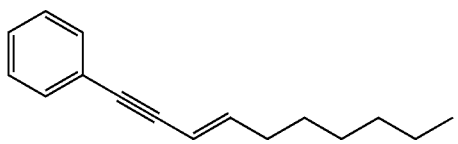

(E)-1-Phenyldec-3-en-1-yne (Table 3, entry 5): The general procedure was used to convert phenylacetylene and (E)-1-iodooctene to the title product in 24 hours. Purification by flash chromatography (light petroleum ether as eluent) gave the analytically pure product as a clear oil (423 mg, 99% yield). $^1$H NMR (400 MHz, CDCl$_3$) δ 7.40 (m, 2H), 7.28 (m, 3H), 6.24 (m, 1H), 5.68 (d, J=15.84, 1H), 2.15 (q, 2H), 1.41-1.28 (m, 8H), 0.89 (t, 3H). $^{13}$C NMR (100 MHz, CDCl$_3$) δ 145.08, 131.24, 128.07, 127.67, 123.49, 109.32, 88.23, 87.68, 33.08, 31.52, 28.66, 28.59, 22.45, 13.94. Anal. Calc'd. for $C_{16}H_{20}$: C, 90.51; H, 9.49; Found C, 90.65; H, 9.58.

Example 4a

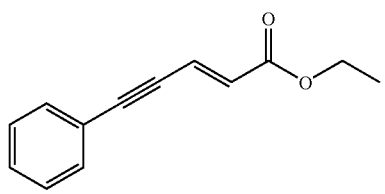

Ethyl (E)-5-phenyl-2-buten-4-ynoate (Table 4 entry 1): The modified procedure was used to convert phenylacetylene and (E)-ethyl-3-iodoacrylate to the title product. GC yield was found to be 74% and 99% after 8 and 24 hours respectively.

Example 4b

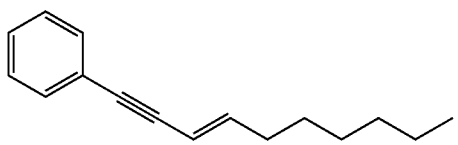

(E)-1-Phenyldec-3-en-1-yne (Table 4, entry 2): The modified procedure was used to convert phenylacetylene and (E)-1-iodooctene to the title product. Purification by flash chromatography (light petroleum ether as eluent) afforded a clear oil (418 mg, 98% yield). The proton spectra obtained matches that of the analytically pure compound previously isolated (see Table 3, entry 5). $^1$H NMR (400 MHz, CDCl$_3$) δ 7.42 (m, 2H), 7.28 (m, 3H), 6.24 (m, 1H), 5.66 (d, J=15.85, 1H), 2.15 (q, 2H), 1.42-1.29 (m, 8H), 0.89 (t, 3H).

Example 4c

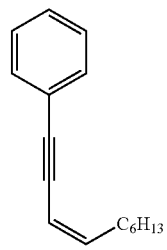

Dec-3-en-1-ynyl-benzene (Table 4, entry 3): The modified procedure was used to convert (Z)-1-Iodo-oct-1-ene and phenyl acetylene to the title product. Purification by flash chromatography (hexane as the eluent) gave the analytically pure product as a colorless oil (420 mg, 98% yield). $^1$H NMR (400 MHz, CDCl$_3$) δ 7.44-7.41 (m, 2H), 7.29-7.27 (m, 3H), 5.99-5.92 (m, 1H), 5.67-5.65 (d, J=10.7, 1H), 2.42-2.36 (m, 2H), 1.46-1.43 (m, 2H), 1.37-1.29 (m, 6H), 0.89-0.86 (m, 3H). $^{13}$C NMR (100 MHz, CDCl$_3$) δ 144.36, 131.42, 128.30, 127.96, 123.82, 109.06, 93.46, 86.57, 31.76, 30.45, 28.96, 28.91, 22.70, 14.16. Anal. Calcd. for $C_{16}H_{20}$: C, 90.51; H, 9.49; Found C, 90.24; H, 9.47.

Example 4d

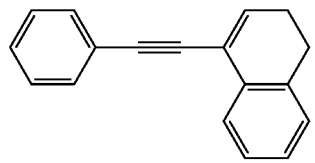

1,2-dihydro-4-(2-phenylethynyl)naphthalene (Table 4, entry 4): The modified procedure was used to convert phenylacetylene and 1,2-dihydro-4-iodonaphthalene to the title product in 24 hours. Purification by flash chromatography (20% CH$_2$Cl$_2$ in hexanes) gave the analytically pure product as a light yellow oil (360 mg, 78% yield). $^1$H NMR (400 MHz, CDCl$_3$) δ 7.68 (d, J=7.58, 1H), 7.52 (m, 2H), 7.31 (m, 3H), 7.25 (m, 1H), 7.18 (t, 1H), 7.13 (d, J=7.33, 1H), 6.54 (t, 1H), 2.80 (t, 2H), 2.42, (m, 2H). $^{13}$C NMR (100 MHz, CDCl$_3$) δ 135.49, 135.05, 132.64, 131.54, 128.29, 128.07, 127.66, 127.39, 126.62, 125.05, 123.43, 121.72, 90.28, 87.29, 27.14, 23.69. Anal. Calc'd. for $C_{18}H_{14}$: C, 93.87; H, 6.13; Found C, 93.79; H, 6.36.

Example 4e

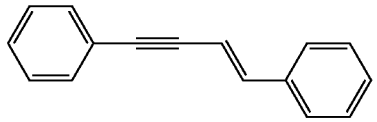

(E)-1,4-diphenylbutenyne (Table 4, entry 5): The modified procedure was used to convert phenyl acetylene and β-iodostyrene to the title product. Purification by flash chromatography (20% $CH_2Cl_2$ in hexanes) gave the analytically pure product as a light yellow solid (399 mg, 98% yield). $^1H$ NMR (400 MHz, $CDCl_3$) δ 7.47 (m, 2H), 7.43 (d, J=7.22, 2H), 7.4-7.27 (m, 6H), 7.03 (d, J=16.24, 1H), 6.37 (d, J=16.24). $^{13}C$ NMR (100 MHz, $CDCl_3$) δ 141.24, 136.31, 131.50, 128.71, 128.60, 128.32, 128.16, 126.29, 123.42, 108.13, 91.75, 88.91. Anal. Calcd. for $C_{16}H_{12}$: C, 94.08; H, 5.92; Found C, 93.96; H, 6.10. m.p.: 97-98° C. (lit: 96-97° C.)

Example 5

Synthetic procedures relating to the compounds of the preceding examples can be modified by way of choice and amount of copper(I) salt, ligand, base and/or solvent utilized, with corresponding modification in preparation of the metal-ligand catalyst complex/compounds. Depending on choice of ligand, vinyl halide and/or acetylene, other useful solvents include dichloromethane, toluene, benzene, NMP, DMF and DMSO. Likewise, the ligands of such catalyst compounds can alternatively comprise components represented by the structures of FIG. 2. The precursors for such components would be known in the art, as would modification in preparation of the corresponding catalyst and resulting enyne product—such modification as can further include choice of base to effect the desired reaction.

Example 6

The synthetic procedures relating to this invention can be modified using various combinations of known Cu(I) complexes or reaction products, bases and solvents, as provided in Table 5. Without limitation, such syntheses (and reagent combinations of Table 5) can also be used to couple any of a number of a wide range of acetylene/vinyl halide combinations, as would be understood by those in the art made aware of this invention.

TABLE 5

| Solvent | Copper(I) Component* | Base |
|---|---|---|
| THF | $Cu(phen)(PPh_3)_2NO_3$ | CsOAc |
| Dioxane | $Cu(phen)PPh_3Br$ | DBU |
| Isopropyl alcohol | $Cu(neocup)PPh_3Cl$ | $K_3PO_4$ |
| Toluene | CuI/neocuproine | $Na_2CO_3$ |
| | $Cu(neocup)PPh_3I$ | NaOtBu |
| | $Cu(neocup)PPh_3Br$ | $K_2CO_3$ |
| | CuI/neocuproine | $Cs_2CO_3$ |
| | CuCl/Phen | NaOtBu |
| | $Cu(bipy)PPh_3Br$ | KOtBu |
| | $[Cu(CH_3CN)]PF_6$ | |
| | $Cu(PPh_3)_3Br$ | |

*Phen = 1,10-phenanthroline;
neocup = 2,9-dimethyl-1,10-phenathroline (neocuproine);
bipy = 2,2'-bipyridine Various other Cu(I) components, in accordance with this invention, useful in the synthesis of 1,3-enynes can be prepared as would be understood in the art with reference to Example 5 and the bi-dentate ligands of FIG. 2.

As shown by the preceding examples and data, the present invention provides a mild, facile synthesis of 1,3-enynes via a copper(I)-catalyzed cross-coupling reaction between an acetylene and a vinyl halide. For most substrates, non-limiting embodiments can employ $[Cu(bipy)PPh_3Br]$ as a catalyst and $K_2CO_3$ as a base. In cases where the vinyl halide is an (E)-alkene, use of a $[Cu(phen)(PPh_3)_2]NO_3$ catalyst and a $Cs_2CO_3$ base provides good results. The methodology tolerates a wide-range of substrates and attendant functional groups, affording the desired enynes in high yields while retaining vinylic stereochemistry and permitting subsequent chemical modification.

We claim:

1. A method of using a Cu(I) compound for 1,3-enyne formation, said method comprising:
    providing an vinyl halide, and an acetylene; and
    contacting at least one of said halide and said acetylene with a Cu(I) component selected from a Cu(I) bi-dentate ligand complex, a reaction product comprising a Cu(I) salt and a bi-dentate ligand and combinations thereof, said method absent a palladium catalyst.
2. The method of claim 1 wherein said Cu(I) component is in an amount less than stoichiometric.
3. The method of claim 2 wherein said bi-dentate ligand is selected from 1,10-phenanthroline and 2,9-dimethyl-1,10-phenanthroline.
4. The method of claim 3 wherein said Cu(I) component comprises a Cu(I) halide and one of said bi-dentate ligands.
5. The method of claim 1 further comprising a base component.
6. The method of claim 1 wherein said acetylene is selected from aryl and alkyl acetylenes.
7. A system for preparation of 1,3-enynes, said system comprising:
    a vinyl halide;
    an acetylene selected from aryl and alkyl acetylenes; and
    a Cu(I) component selected from a Cu(I) bi-dentate ligand complex, and a reaction product comprising a Cu(I) salt and a bi-dentate ligand, said Cu(I) component present in an amount less than stoichiometric, said system absent a palladium catalyst.
8. The system of claim 7 comprising a catalytic amount of said Cu(I) component.
9. The system of claim 7 wherein said bi-dentate ligand is selected from 1,10-phenanthroline and 2,9-dimethyl-1,10-phenanthroline.
10. The system of claim 9 wherein said Cu(I) component comprises a chelation product of a Cu(I) halide and one of said bi-dentate ligands.
11. The system of claim 7 further comprising a solvent.
12. The system of claim 7 further comprising a base component.
13. A method for coupling vinyl halides and acetylenes, said method comprising:
    providing a vinyl halide compound;
    providing an acetylene compound, said acetylene compound selected from alkyl acetylenes, aryl acetylenes and heterocyclic acetylenes; and
    contacting said vinyl and acetylene compounds with a medium comprising a Cu(I) component selected from a Cu(I) bi-dentate ligand complex and a reaction product of a Cu(I) salt and a bi-dentate ligand, said Cu(I) component in an amount less than stoichiometric, and said medium further comprising a solvent component, said method absent a palladium catalyst.
14. The method of claim 13 wherein said vinyl halide is selected from cyclic and acyclic vinyl iodides.
15. The method of claim 13 wherein said acetylene is selected from alkyl and aryl acetylenes.
16. The method of claim 13 wherein said bi-dentate ligand is selected from 1,10-phenanthroline and 2,9-dimethyl-1,10-phenanthroline.
17. The method of claim 16 wherein said Cu(I) component is selected from $Cu(phen)(PPh_3)_2NO_3$ and a CuI/neocuproine reaction product.

18. The method of claim 17 wherein said solvent is selected from toluene and isopropyl alcohol.

19. The method of claim 18 wherein said medium further comprises a base component.

20. The method of claim 19 wherein said base component is $K_3PO_4$.

* * * * *